United States Patent
Yu et al.

(10) Patent No.: US 11,971,374 B2
(45) Date of Patent: *Apr. 30, 2024

(54) IN SITU, REAL-TIME IN-LINE DETECTION OF FILLING ERRORS IN PHARMACEUTICAL PRODUCT MANUFACTURING USING WATER PROTON NMR

(71) Applicant: UNIVERSITY OF MARYLAND, BALTIMORE, Baltimore, MD (US)

(72) Inventors: Yihua (Bruce) Yu, Ellicott City, MD (US); Marc B. Taraban, North Potomac, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,233

(22) Filed: Jan. 3, 2023

(65) Prior Publication Data

US 2023/0152256 A1 May 18, 2023

Related U.S. Application Data

(60) Division of application No. 17/030,088, filed on Sep. 23, 2020, now Pat. No. 11,543,371, which is a continuation-in-part of application No. 16/593,145, filed on Oct. 4, 2019, now Pat. No. 11,585,770.

(60) Provisional application No. 63/010,127, filed on Apr. 15, 2020, provisional application No. 62/741,142, filed on Oct. 4, 2018.

(51) Int. Cl.
*G01N 24/08* (2006.01)
*G01N 33/15* (2006.01)
*G01R 33/46* (2006.01)

(52) U.S. Cl.
CPC ......... *G01N 24/084* (2013.01); *G01N 24/085* (2013.01); *G01N 33/15* (2013.01); *G01R 33/46* (2013.01)

(58) Field of Classification Search
CPC .... G01N 24/082; G01N 33/15; G01N 24/085; G01N 24/084; G01R 33/448; G01R 33/46
See application file for complete search history.

(56) References Cited

U.S. PATENT DOCUMENTS

| 6,307,372 B1 | 10/2001 | Sugarman et al. |
| 8,314,618 B2 | 11/2012 | Bieri et al. |
| 8,854,038 B2 | 10/2014 | Hernando et al. |

(Continued)

OTHER PUBLICATIONS

Baroni, et al. Relaxometric Characterization of Balsamic Vinegar, meeting abstract 6th Conference on Field Cycling NMR Relaxometry Turin (Italy) Jun. 4, 2009.

(Continued)

*Primary Examiner* — Jay Patidar
(74) *Attorney, Agent, or Firm* — Tristan A. Fuierer; Casimir Jones, SC (57) ABSTRACT

A method of using the transverse relaxation time ($T_2$) of solvent NMR signal to detect filling errors of an alum-containing product in real-time and in-line during manufacturing, for example during a fill-finish unit operation. This method can be used for quality control in vaccine manufacturing to ensure the delivery of the correct concentration of alum-containing product to the product container such as a vial or pre-filled syringe.

13 Claims, 4 Drawing Sheets

(56) References Cited

U.S. PATENT DOCUMENTS

| | | | |
|---|---|---|---|
| 8,862,407 | B2 | 10/2014 | Chugunov et al. |
| 9,194,925 | B2 | 11/2015 | Zhong et al. |
| 10,267,754 | B2 | 4/2019 | Yu et al. |
| 10,514,347 | B2 | 12/2019 | Yu et al. |
| 11,543,371 | B2 | 1/2023 | Yu et al. |
| 11,585,770 | B2 | 2/2023 | Yu et al. |
| 2004/0090231 | A1 | 5/2004 | Augustine et al. |
| 2005/0287527 | A1 | 12/2005 | Ni et al. |
| 2006/0269965 | A1 | 11/2006 | Josephson |
| 2007/0116602 | A1 | 5/2007 | Lee |
| 2007/0152666 | A1 | 7/2007 | Thesen |
| 2009/0179644 | A1* | 7/2009 | Bons .................. G01K 11/006 324/315 |
| 2010/0047180 | A1 | 2/2010 | Zeng et al. |
| 2010/0072994 | A1 | 3/2010 | Lee et al. |
| 2010/0278829 | A1 | 11/2010 | Edwards, III et al. |
| 2011/0124744 | A1 | 5/2011 | Lee et al. |
| 2012/0100546 | A1 | 4/2012 | Lowery, Jr. et al. |
| 2012/0164644 | A1 | 6/2012 | Neely et al. |
| 2013/0244238 | A1 | 9/2013 | Neely et al. |
| 2013/0265054 | A1 | 10/2013 | Lowery, Jr. |
| 2016/0047761 | A1 | 2/2016 | Yu et al. |
| 2017/0176359 | A1 | 6/2017 | Graessl et al. |
| 2018/0052122 | A1 | 2/2018 | Davis et al. |
| 2018/0113141 | A1 | 4/2018 | Lowery, Jr. et al. |
| 2019/0293579 | A1 | 9/2019 | Yu et al. |
| 2019/0391218 | A1 | 12/2019 | Yu et al. |

OTHER PUBLICATIONS

Baylor, N.W et al.(2002) Aluminum salts in vaccines—US perspective. Vaccine, 20, S18-S23.

Bloembergen, N. et al.; Relaxation Effects in Nuclear Magnetic Resonance absorption, Phys. Rev. 1948:73;679-712.

Bouchoux, Antoine et al. Molecular Mobility in Dense Protein Systems: An Investigation through 1 H NFM Relaxometry and Diffusometry, Journal of Physical Chemistry Part B: Condensed Matter, Materials, Surfaces, Interfaces & Biophysical, 2012:116(38):1744-11753.

Briggs, K.T. et al. Water proton NMR detection of amide hydrolysis and diglycine dimerization. Chem. Comm. 2018:54:7003-7006.

Daskiewicz, O. et al. Proton Magnetic Relaxation and Protein Hydration. Nature, 1963:200(4910):1006-1007.

Dalvit, C. et al. High-Throughput NMR-Based Screening with Competition Binding Experiments, J. Am. Chem. Soc., 2002:124;7702-7709.

Fanali, G. et al.; Human serum albumin: From bench to bedside, Mol. Asp. med., 2012:33;209-290.

Farrell, C, et al. Analytical Control Strategies for Aluminum, Vaccine Analytical Development, 2014, 1-29.

Feng, Y. et al. Linear dependency of NMR relaxation rates on shear modulus in hydrogels. Soft Matter, 2011:7:9890-9893.

Feng, Y. et al. Water Proton NMR—A Sensitive Probe for Solute Association, Chem. Commun., 2015:51:6804-6807.

Guo, J. et al. The Effect of Shipping Stresses on Vaccine Redispersion Time. Journal of Pharmaceutical Sciences, 2016:105:2009-2013.

International Search Report and Written Opinion, dated Feb. 20, 2018.

Joint WHO-UNICEF Statement 2, Apr. 2010, Who Recommends Recall and Destruction of All Lots of SHAN5 Vaccine as a Precautionary Measure, pp. 1-3.

Kartoglu, U. et al. Validation of the shake test for detecting freeze damage to adsorbed vaccine. Bull. World Health Organ. 2010:88:624-631.

Khatun, R. et al. 27Al and 31P Nmr spectroscopy method development to quantify aluminum phosphate in adjuvanted vaccine formulations. Journal of Pharmaceutical and Biomedical Analysis, 2018:159:166-172.

Korzhnev, D. et al.; Probing Invisible, Low-Populated States of Protein Molecules by Relaxation Dispersion NMR Spectroscopy: An Application to protein Folding. Acc. Chem. Res., 2008:41:442-451.

Krayukhina, E., et al.; Aggregation analysis of pharmaceutical human immunoglobulin preparations using size-exclusion chromatography and analytical ultracentrifugation sedimentation velocity, J. Biosci. Bioeng. 2012:115:104-110.

Levi, M. et al., The Fluad Case in Italy: Could it have been dealt differently? Human Vaccines & Immunotherapeutics, 2017:13:379-384.

Lewis, L. M et al. Ex Situ and In Situ Characterization of Vaccine Suspensions in Pre-Filled Syringes. Journal of Pharmaceutical Sciences, 2017:106:2163-2167.

Lindblad, E.B. Aluminum compounds for use in vaccines. Immunology and Cell Biology, 2004:82:497-505.

Mahler, Hans-Christian et al. Protein aggregation: Pathways, induction factors and analysis, Journal of Pharmaceutical Sciences, 2009:98(9):2909-2925.

Mao, X et al.; Understanding Radiation Damping in a Simple Way, Concepts Magn. Reson. 1997:9:173.

Metz, H. et al.; Benchtop-NMR and MRI—A new analytical tool in drug delivery research, Int. J. Pharm. 2008:364:70-175.

Mishra, A. et al. Standardization and validation of a new atomic absorption spectroscopy technique for determination and quantitation of Aluminium adjuvant in immunobiologicals. Biologicals, 2007:35:277-284.

Muthurania, K. et al. Investigation of the sedimentation behavior of aluminum phosphate: influence of pH, ionic strength, and model Antigens. Journal of Pharmaceutical Sciences, 2015:104:3770-3781.

Notice of Allowance for U.S. Appl. No. 16/369,534.

Oliva, A. et al.; Influence of temperature and shaking on stability of insulin preparations: degradation kinetics, Int. J. Pharm., 1996:143:163-170.

Petrovsky, Nikolai; Vaccine adjuvant safety: the elephant in the room, Expert Review of Vaccines, 2013:12:715-717.

Petrovsky, N. Comparative safety of vaccine adjuvants: a summary of current evidence and future needs. Drug Safety, 2015:38:1059-1074.

Rohrer, M et al. Comparison of magnetic properties of MRI contrast media solutions at different magnetic field strengths. Invest. Radiol. 2005:40:715-724.

Saso, L. et al.; Effect of Selected Substances on Heat-Induced Aggregation of Albumin, IgG and Lysozyme, Res. Commun. Pathol. Pharmacol. 1998:102:5-28.

Signorelli, C. et al. Dramatic 2015 excess mortality rate in Italy: a 9.1% increase that needs to be explained. Scand. J. Public Health, 2015:44:549-550.

Taraban, M.B. et al. Water Proton NMR for In Situ Detection of Insulin Aggregates, J. Pharm. Sci., 2015:104:4132-4141.

Taraban M.B. et al. Water Proton NMR: A Tool for Protein Aggregation Characterization, Anal. Chem., 2017:89:5494-5502, DOI: 10.1021/acs.analchem.7b00464.

Taraban, M.B. et al. Non-invasive detection of nanoparticle clustering by water proton NMR. Transl. Mater. Res. 2017b:4:025002.

Taraban, Marc B., et al.; Accessing Aluminum Vaccine Adjuvant Filling, Sedimentation, and Resuspension in Sealed Vials using Water Proton NMR, American Pharmaceutical Review, 2019:70-73.

Weerasekare, G.M. et al. Sol and gel states in peptide hydrogels visualized by Gd(III)- enhanced MRI. Biopolymers (Pept. Sci.) 2011:96:734-743.

Vecchi, S. et al. Aluminum adjuvant dose guidelines in vaccine formulation for preclinical evaluations. J. Pharm. Sci. 2011:101:17-20.

Yu, Bruce et al. Water Proton NMR for Noninvasive Chemical Analysis and Drug Product Inspection,: American Pharmaceutical Review, 2017:20:34-39.

* cited by examiner

IN SITU, REAL-TIME IN-LINE DETECTION OF FILLING ERRORS IN PHARMACEUTICAL PRODUCT MANUFACTURING USING WATER PROTON NMR

CROSS REFERENCE TO RELATED APPLICATIONS

This application is a divisional of U.S. patent application Ser. No. 17/030,088, filed on Sep. 23, 2020, which is a continuation-in-part of U.S. patent application Ser. No. 16/593,145, filed on Oct. 4, 2019, which claims priority to U.S. Provisional Patent Application No. 62/741,142 filed on Oct. 4, 2018 in the name of Yihua (Bruce) Y U et al. and entitled "In Situ Determination of Alum Filling Evenness and Sedimentation in Pharmaceutical Products using Water Proton NMR," which are hereby incorporated by reference herein in their entirety. U.S. patent application Ser. No. 17/030,088 also claims priority U.S. Provisional Patent Application No. 63/010,127 filed on Apr. 15, 2020 in the name of Yihua (Bruce) Y U et al. and entitled "Real-Time In Situ Monitoring of Drug Product Degradation Using Water Proton NMR," which is hereby incorporated by reference herein in its entirety.

STATEMENT OF FEDERAL SUPPORT

This invention was made with government support under Contract No. 75F40119C10104 awarded by the Food and Drug Administration. The government has certain rights in the invention.

FIELD

The present invention relates to methods for noninvasive in-line quality control of alum-containing products, including vaccines comprising an alum adjuvant, using solvent nuclear magnetic resonance (NMR).

DESCRIPTION OF THE RELATED ART

Adjuvants play a critical role in the efficacy of vaccines. The most widely used vaccine adjuvants are aluminum salt particles, more commonly referred to as alum. Presently, more than 20 vaccines contain an alum adjuvant, including the anthrax, DTaP, DTaP/Hepatitis B/Polio, DTaP/Polio, DTaP/Polio/Hib, Hib, Hepatitis A, Hepatitis A/Hepatitis B, Hepatitis B, HPV, Meningococcus B, Pneumococcus, Tetanus and Diptheria Toxoids Adsorbed, TdaP, and the Diphtheria and Tetanus Toxoids Adsorbed vaccines. It should be expected that some or all vaccines used to inoculate against coronaviruses and more specifically severe acute respiratory syndrome coronavirus 2 (SARS-CoV-2), which causes the respiratory illness known as the novel coronavirus disease 2019 (COVID-19), may comprise an alum adjuvant.

The most commons aluminum salts include aluminum hydroxide, aluminum phosphate, and aluminum hydroxyphosphate sulfate [Baylor, 2002]. Alum salt particles are micron-sized with certain size heterogeneity [Lindblad, 2004]. Adjuvant dose in released products is related to vaccine safety and efficacy and adjuvant toxicity is of concern to vaccine safety [Petrovsky, 2015].

Alum-adjuvanted vaccines are formulated as liquid suspensions. The last step of the manufacturing process is the fill-finish unit operation. This step includes mixing of the concentrated suspension with diluent solution and filling the diluted suspension into vials or pre-filled syringes. If mixing or filling is not done properly, the concentration of the aluminum particles (with or without antigen) can be wrong. For example, during filling, the line can get clogged by the aluminum salt particles, which results in an incorrect flow rate and eventually filling error. Non-homogeneous mixing during manufacturing affects the concentration of aluminum particles and can also lead to the uneven filling of vials. Vaccines having too much, or too little alum adjuvant can lead to less than optimal immune responses in immunized subjects (too much may cause harm while too little may be ineffective).

Filling levels of alum-adjuvanted vaccines are currently determined using atomic absorption microscopy [Mishra, 2007] or $^{27}$Al/$^{31}$P NMR spectroscopy [Khatun, 2018]. These ex situ techniques are destructive, as they require taking the drug substance out of its container, and perturbative (as they require dilution, pH adjustment, and other sample preparation steps). They also require ten minutes or longer for data acquisition as well as highly trained personnel for analysis. Additionally, none of these techniques could be used to provide real-time in-line monitoring of the filling levels of alum-adjuvanted vaccines.

There is a need for a fast and reliable technique which can be used for quality control in vaccine manufacturing, for example, to monitor the aluminum concentration and the flow rate in real-time in-line settings, without interrupting the flow. Towards that end, the present invention relates to a method of using the transverse relaxation rate ($R_2$) of the solvent NMR signal, e.g., $R_2(^1H_2O)$, to determine the flow rate and alum particle concentration in situ and in real-time in-line. Using flow-wNMR, as described herein, it is possible to determine if a mixing or filling error occurred during vaccine manufacturing (e.g., during the fill-finish unit operation), in real-time, in contact-free in-line settings, using low cost instrumentation, simple and rapid data acquisition and analysis, and minimal technical expertise requirement.

SUMMARY

The present invention generally relates to a method of using NMR relaxation rates, specifically the transverse relaxation rate constant $R_2$ of solvent molecules, e.g., water, to determine if a filling error occurred during the manufacturing process of alum-containing products, for example during the fill-finish unit operation.

In one aspect, a method of detecting a filling error of an alum-containing product in real-time in-line during a fill-finish unit operation is described, said method comprising:
flowing the alum-containing product into a filling conduit, wherein the filling conduit directs the alum-containing product into a vial, and wherein the filling conduit is arranged to flow through a magnet and a probe of nuclear magnetic resonance (NMR) spectrometer prior to the vial;
measuring the transverse relaxation rate of solvent $R_{2,m}$ in the alum-containing product flowing through the filling conduit; and
comparing the measured $R_{2,m}$ to a reference transverse relaxation rate of solvent $R_{2,r}$, wherein the reference $R_{2,r}$ represents an acceptable flow rate or concentration of aluminum particles in the alum-containing product, wherein when the measured $R_{2,m}$ is inside a range of the reference $R_{2,r}$, there is no filling error.

Other aspects, features and advantages of the invention will be more fully apparent from the ensuing disclosure and appended claims.

DETAILED DESCRIPTION, AND PREFERRED EMBODIMENTS THEREOF

The present invention generally relates to a method of using NMR relaxation rates, specifically the transverse relaxation rate constant $R_2$ of solvent molecules, e.g., water, to determine if a mixing or a filling error occurred during manufacturing (e.g., during the fill-finish unit operation), in real-time and in contact-free in-line settings.

Advantageously, the method described herein is a reliable and simple method and has application as an in-line quality control tool for any manufacturing process utilizing alum-containing products, e.g., vaccine manufacturing. The method enables the non-destructive assessment of the alum-containing products, formulated as aqueous suspensions, without interrupting the flow during filling, by measuring the transverse nuclear spin relaxation rate constant, $R_2$, of a solvent, e.g., water under flow conditions. There is no drawing of any sample out of the flow loop and there is no physical contact between the NMR instrument and the aluminum particle suspension, which stays inside a closed loop that passes through the NMR magnet/probe.

Continuous manufacturing of drugs and vaccines is one of the priorities of the pharmaceutical industry, but widespread implementation is hampered by a lack of noninvasive/nondestructive process analytical technology (PAT) systems capable of real-time, in-line monitoring of parameters, such as concentration and/or flow rate. The present inventors have explored the potential of water proton NMR under flow conditions (flow-wNMR), using $R_2(^1H_2O)$ as a quantitative indicator of the concentration and flow rate of alum-containing products under flow conditions.

In the present invention, wNMR under flow conditions (flow-wNMR) is described as a contact-free in-line PAT with demonstrative usefulness for alum-containing product manufacturing, for example during the fill-finish unit operation. A custom-made flow NMR instrument (see, FIG. 1) was developed to analyze the changes of $R_2(^1H_2O)$ due to changes of flow rate or concentration under flow.

There is no bypass system and no stop-flow cell. The results demonstrate that flow-wNMR could be used as a contact-free in-line PAT to monitor the filling of alum-containing products under flow conditions.

The present inventors previously disclosed that uneven filling levels of alum particles or the sedimentation of same in the product containers (e.g., vials) are evidenced by a variation, either an increase or a decrease, of the transverse nuclear spin relaxation rate constant, $R_2$, of water, relative to a known control, as provided by the manufacturer. Thereafter, as new batches of alum-containing products are prepared, the $R_2$ constant of water of each new batch can be measured by the manufacturer to confirm the even filling of alum particles in the product containers (e.g., vials) before releasing same for sale and purchase. If the measured $R_2$ constant of the tested alum-containing product is outside of the reference range provided by the manufacturer, meaning that the vaccine dose is either too high or too low due to uneven alum particle filling, the specific vial containing the tested alum-containing product should be rejected. Further, the $R_2$ constant of water can be measured by the purchaser/user before use to confirm an acceptable resuspension of the alum particles in the alum-containing products pursuant to the manufacturer's guidelines. If the measured $R_2$ constant of the resuspended alum-containing product is outside of the reference range provided by the manufacturer, meaning that there was unacceptable resuspension, the tested alum-containing product should be rejected.

The present invention describes the use of flow wNMR to determine if a filling error occurred during manufacturing, specifically during the fill-finish unit operation. Using flow wNMR, the $R_2$, of water of the alum-containing product being introduced to product containers (e.g., vials) can be determined in real-time in-line under flow conditions. For example, if the measured $R_2$ constant of the tested alum-containing product doesn't correspond to the expected $R_2$ constant of the alum-containing product at the preferred flow rate, there may be a clog in the filing apparatus or the concentration of aluminum in the alum-containing product is incorrect, suggesting that there is inadequate mixing of the alum-containing product upstream of the fill-finish unit operation and/or accidental exposure of the alum-containing product to at least one stressor. Either will result in the product in a product container (e.g., vial) having the incorrect concentration of aluminum particles (with or without antigen), which relates to vaccine dose and potency Advantageously, using flow wNMR, these measurements can be performed using a simple apparatus coupled with a handheld or desktop NMR, with no drawing of any alum-containing product out of the filling conduit and no physical contact between the NMR instrument and the alum-containing product, passes through the filling conduit, which that passes through the NMR magnet.

Figure 1:
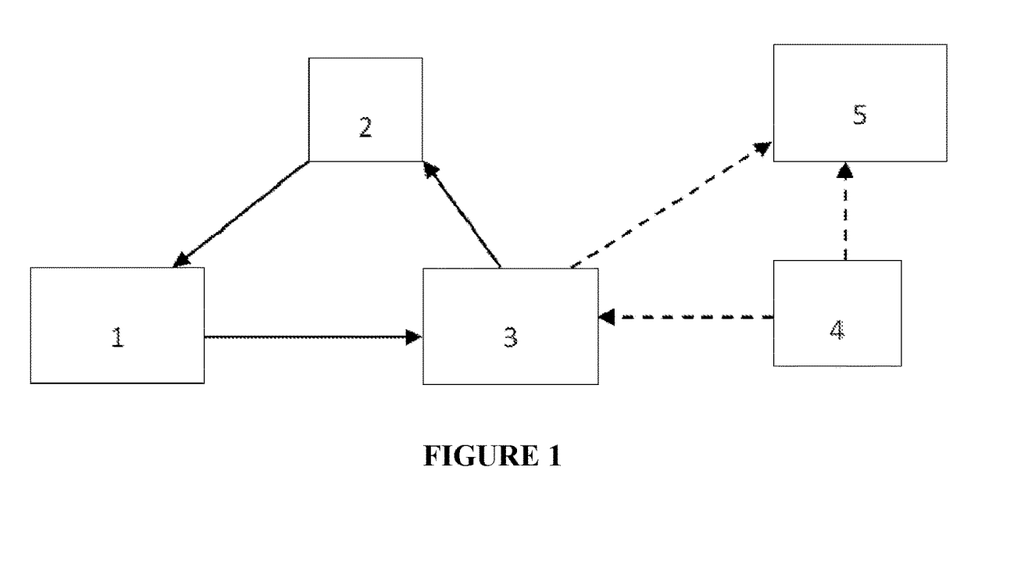
FIG. 1 is a photo of the flow NMR measurement apparatus.

FIG. 1 is an image of an embodiment of a flow wNMR apparatus, said apparatus comprising (1) a peristaltic pump; (2) a sample reservoir (50 mL centrifuge tube); (3) magnet with flow tube inserted; (4) magnet thermostat with spectrometer console; and (5) control and data processing PC.

The person skilled in the art can readily envision the placement of an apparatus at a location in the fill-finish unit operation such that the filling conduit passes through the magnet (3) prior to delivery of the alum-containing product to a product container (e.g., vial). Flow wNMR apparatuses can be purchased from Resonance Systems, GmbH, Kirchheim/Teck, Germany.

Reference herein to alum-containing products can include vaccines comprising an alum adjuvant as well as pharmaceuticals comprising aluminum particles.

Recent breakthrough developments in the instrumentation for nuclear magnetic resonance (NMR) spectroscopy and imaging have opened up opportunities to design novel nondestructive analytical techniques for the nanoparticle industry. The analytical procedures become significantly faster with the application of commercially available computer-controlled NMR autosamplers. Of special importance was the appearance of commercially available, relatively inexpensive benchtop NMR and magnetic resonance imaging (MRI) instruments and relaxometers [Metz, 2008]. Benchtop NMR instruments enable highly accurate measurements of nuclear spin relaxation times $T_1$ and $T_2$. Moreover, most of these instruments have a permanent or electronically cooled magnet with the variable bore from 10 mm to 45 mm and even larger which provides a great flexibility in the nonintrusive measurements of vials of various sizes. Other known portable and handheld NMR instruments are known in the art and can be used to practice the methods described herein.

The present inventors have previously shown that water proton NMR (wNMR) monitors water, which acts as a reporter for analytes dissolved in it. As a reporter, water has two tremendous advantages. First, its concentration far surpasses that of any analyte dissolved in it, by $10^3$-$10^6$ fold in most cases. This makes the $^1H_2O$ signal easily detectable by benchtop and other portable NMR instruments. Further, the solute association can be detected through the solvent NMR signal. Second, water is "endogenous" to all biomanufacturing processes and all biologic products, including vaccines. This sets it apart from "exogenous" reporters such as fluorescent dyes or radiotracers. The high concentration of "endogenous" water makes it possible for wNMR to be contact-free in situ.

As defined herein, a "particle" corresponds to particles between about 1 nanometer and 50 microns in diameter, including particles that would be traditionally characterized as nanoparticles (e.g., about 1 nm to about 100 nm) and particles that would be traditionally characterized as micron-sized (e.g., up to about 10 microns). Particle size ranges relevant to the present invention include about 500 nm to about 1000 nm, about 1000 nm to about 5000 nm (5 microns), and about 1000 nm to about 10000 nm (10 microns). A person with an ordinary skill in the art will readily understand that the above particle size range is intended to be unlimited and could be extended to smaller and/or larger sizes. Also, it should be appreciated that the particles can be any shape, including spherical, can be substantially symmetrical or asymmetrical, and/or can be a single particle or be present as an aggregate of particles having an average aggregate size in a range from about 100 nm to about 10 microns or about 500 nm to about 1000 nm, about 1000 nm to about 5000 nm (5 microns), or about 1000 nm to about 10000 nm (10 microns). It should be understood by the person skilled in the art that the "particles" can be free aluminum particles or aluminum-antigen complexes, or a mixture of free aluminum particles and aluminum-antigen complexes.

As defined herein, the "alum-containing product" includes a product with nano- and micron-sized particles comprising aluminum and suspended in a solvent or a mixture of solvents. The alum-containing product can further comprise at least one surfactant, at least one water-soluble organic solvent, at least one dispersant, at least one biocide, at least one buffering agent, at least one pH adjusting agent (e.g., acids and/or bases), with or without antigens, or any combination thereof, as readily determined by the person skilled in the art. Many vaccines are alum-containing products because of the presence of an aluminum adjuvant.

As defined herein, a "vial" corresponds to a container, vessel, bottle, syringe (e.g., a pre-filled syringe), injection pen, or ampoule used to store the vaccine or other alum-containing product, wherein the vial comprises glass, plastic, ceramic, rubber, elastomeric material, and/or anything non-magnetic metal. The vial can have a screw top, a top that is closed using a cork or plastic stopper, a crimp vial (closed with a rubber stopper and a metal cap), a flip-top, a snap cap, or any other article of manufacture used to seal or close a vial. The vial can be tubular or cylindrical or have a bottle-like shape with a neck. Other types and shapes of vials used to store particles as well as caps are readily understood by the person skilled in the art.

It is understood by the person skilled in the art that the "measuring" of the transverse relaxation rate of solvent $R_2$ is may be done by measuring some other parameter and converting to the $R_2$ value.

As defined herein, a "non-destructive" or "contact-free" measurement is defined as a measurement performed without withdrawing, or directly contacting, any sample from the filling conduit or tube. It is understood by the person skilled in the art that the "filling conduit or tube" is used during the fill-finish unit operation to deliver products from an upstream large-scale product vessel to the product container (e.g., vial). Notably, the filling conduit or tube can be optically transparent or not optically transparent. Given the fact that the method described herein corresponds to the fill-finish unit operation, it goes without saying that a non-destructive or contact-free measurement means that no additives or probes or the like are added prior to the measurement of the transverse relaxation rate of solvent $R_2$ in the alum-containing product.

As defined herein, "alum" corresponds to aluminum-containing salts comprising one or more of aluminum hydroxide, aluminum phosphate, alum ($KAl(SO_4)·12H_2O$), aluminum hydroxyphosphate sulfate, as well as other known or proprietary aluminum salts that can be used as an alum adjuvant or in pharmaceutical products comprising aluminum.

As defined herein, "DS" is a drug substance, which refers to the bulk drug solution or suspension or emulsion.

As defined herein, "DP" is a drug product, which is the combination of the DS plus the container or vial. In other words, DP refers to filled (partially or fully), sealed and labeled vials comprising the DS.

Suspensions and emulsions have complex hydrodynamic behavior, which might complicate the very last step of product manufacturing, the fill-finish step. For example, alum particles may become clogged in the filling conduit or tube, which may lead to uneven filling of vials from the batch. For example, if the concentration of alum particles in the vial is expected to be a mean value of x mg/mL, then the concentration of the alum particles in the filling conduit or tube must also be present at a mean value of x mg/mL±5% of the mean. If the alum particle concentration isn't consistent throughout the filling process, then the alum-containing product in the vials have too much or too little alum. More precisely, too much alum may cause harm while too little may render the alum-containing product, e.g., the vaccine, ineffective. Accordingly, if the alum particle concentration isn't consistent, meaning that a filling error occurred, then the filling process is not in compliance with the quality control specifications. Notably, the method of using flow wNMR, as described herein, can be used to determine alum concentration and flow rate directly, as well as monitor the consistency in the alum concentration and flow rate in the filling conduit or tube in situ and in real-time in-line.

The method described herein can also identify changes in the concentration of aluminum in the alum-containing product just prior to filling of the product containers. There are a variety of stressors including, but not limited to, temperature fluctuations, pH changes, inadequate or vigorous mixing, ionic strength changes, the presence of contaminants, and freezing. The method of using flow wNMR, as described herein, can quantitate the concentration of aluminum directly, as well as monitor the consistency in the concentration over time during the fill-finish unit operation in situ and in real-time in-line.

As defined herein, "filling error" or "filling errors" include, but are not limited to, clogs in the filling conduit, leaks in the filling conduit, pump failure, and manual or automatic computer errors that result in errors such as incorrect flow rates. In addition, for the purposes of the instant application, other production errors that occur just upstream of the filling conduit are being defined as a "filling error" or "filling errors," including, but not limited to, inadequate mixing upstream of the filling conduit, and/or accidental exposure of the alum-containing product to at least one stressor such as temperature fluctuations, pH changes, vigorous mixing, ionic strength changes, the presence of contaminants, and freezing. The filling errors lead to variations of the concentration of aluminum in the product containers (e.g., vials) comprising the alum-containing products prepared for distribution and use.

The present inventors have surprisingly discovered that flow wNMR can be used to monitor and detect filling errors of alum-containing products, e.g., vaccine products, during the fill-finish unit operation. The method can be used with continuous or non-continuous (batch) manufacturing in real-time in-line. In addition to being contact-free, additional advantages of low field solvent NMR includes low cost instrumentation (e.g., a desktop or handheld NMR), simple and rapid data acquisition and analysis, minimal technical expertise, and results that are readily available within <5 min. It should be appreciated that the measurements can occur destructively as well, whereby the sample is withdrawn during the fill-finish unit operation, as readily determined by the person skilled in the art. Further, the method described herein can utilize high field NMR, if needed.

In practice, manufacturers of alum-containing products would typically be interested in the methods described herein. The flow wNMR apparatus is simple to setup and the obtainment of the $R_2(^1H_2O)$ values is well known in the art. The manufacturer will understand how to prepare and use calibration curves, for example, those show in FIGS. 2(a)-3(b) described herein.

Accordingly, in a first aspect, a method of detecting a filling error of an alum-containing product in real-time in-line during a fill-finish unit operation is described, said method comprising: flowing the alum-containing product into a filling conduit, wherein the filling conduit directs the alum-containing product into a vial, and wherein the filling conduit is arranged to flow through a magnet and a probe of nuclear magnetic resonance (NMR) spectrometer prior to the vial;
measuring the transverse relaxation rate of solvent $R_{2,m}$ in the alum-containing product flowing through the filling conduit; and
comparing the measured $R_{2,m}$ to a reference transverse relaxation rate of solvent $R_{2,r}$, wherein the reference $R_{2,r}$ represents an acceptable flow rate or concentration of aluminum particles in the alum-containing product, wherein when the measured $R_{2,m}$ is inside a range of the reference $R_{2,r}$, there is no filling error.

The transverse relaxation rate of solvent $R_2$ can be determined using solvent NMR, preferably low-field solvent NMR. The measuring of the transverse relaxation rate of solvent $R_2$ in the alum-containing product is done using flow wNMR, wherein the flow wNMR apparatus is positioned at a location in the fill-finish unit operation such that the filling conduit passes through the NMR magnet/probe prior to delivery of the alum-containing product to a product container (e.g., vial). This permits the manufacturer to determine, in situ and in real-time in-line, in a contact-less process, if a filling error has occurred. The reference $R_{2,r}$ range, at a specified temperature, is known by the manufacturer for the alum-containing product. Preferably $R_{2,m}$ is measured at substantially the same temperature as $R_{2,r}$. If the measured $R_{2,m}$ is outside of the acceptable range known by the manufacturer, a filling error has occurred. Filling errors include, but are not limited to, clogs in the filling conduit, inadequate mixing upstream of the filling conduit, and/or accidental exposure of the alum-containing product to at least one stressor such as temperature fluctuations, pH changes, vigorous mixing, ionic strength changes, the presence of contaminants, and freezing. It should be appreciated that if a filling error has been identified, the manufacturer can attempt to remedy the error prior to filling any more vials or product containers with the alum-containing product, as readily understood by the person skilled in the art. The method can be used with continuous or non-continuous (batch) manufacturing. For example, the fill-finish unit operation can be continuous or non-continuous (batch).

It should be appreciated that the transverse relaxation time $T_2$, which is the inverse of the transverse relaxation rate $R_2$, can be used as the reference instead and the manufacturer compares the transverse relaxation time of solvent $T_2$ of the alum-containing product to determine if a filling error has occurred, as readily understood by the person skilled in the art. For example, in one embodiment of the first aspect, a method of detecting a filling error of an alum-containing product in real-time in-line during a fill-finish unit operation is described, said method comprising:
flowing the alum-containing product into a filling conduit, wherein the filling conduit directs the alum-containing product into a vial, and wherein the filling conduit is arranged to flow through a magnet and a probe of nuclear magnetic resonance (NMR) spectrometer prior to the vial;
measuring the transverse relaxation time of solvent $T_{2,m}$ in the alum-containing product flowing through the filling conduit; and
comparing the measured $T_{2,m}$ to a reference transverse relaxation time of solvent $T_{2,r}$, wherein the reference $T_{2,r}$ represents an acceptable flow rate or concentration of aluminum particles in the alum-containing product, wherein when the measured $T_{2,m}$ is inside a range of the reference $T_{2,r}$, there is no filling error.

The transverse relaxation time of solvent $T_2$ can be determined using solvent NMR, preferably low-field solvent NMR. The measuring of the transverse relaxation time of solvent $T_2$ in the alum-containing product is done using flow wNMR, wherein the flow wNMR apparatus is positioned at a location in the fill-finish unit operation such that the filling conduit passes through the NMR magnet/probe prior to delivery of the alum-containing product to a product container (e.g., vial). This permits the manufacturer to determine, in situ and in real-time in-line, in a contact-less process, if a filling error has occurred. The reference $T_2$, range, at a specified temperature, is known by the manufacturer for the alum-containing product. Preferably $T_{2,m}$ is measured at substantially the same temperature as $T_{2,r}$. If the measured $T_{2,m}$ is outside of the acceptable range known by the manufacturer, a filling error has occurred. Filling errors include, but are not limited to, clogs in the filling conduit, inadequate mixing upstream of the filling conduit, and/or accidental exposure of the alum-containing product to at least one stressor such as temperature fluctuations, pH changes, vigorous mixing, ionic strength changes, the presence of contaminants, and freezing. It should be appreciated that if a filling error has been identified, the manufacturer can attempt to remedy the error prior to filling any more vials or product containers with the alum-containing product, as readily understood by the person skilled in the art. The method can be used with continuous or non-continuous (batch) manufacturing.

An example of the advantages associated with the methods described herein are as follows. The maximum allowed aluminum dose is 0.85 mg Al(III), according to the US Code of Federal Regulations [Vecchi, 2011]. The highest concentration of Al(III) in FDA-approved vaccines on the market is 1.2 mg/mL in BIOTHRAX. BIOTHRAX is packaged as 5-mL multi dose vials, wherein each dose is 0.6 mg/mL, below the federal limit of 0.85 mg/mL. The alum adjuvant in BIOTHRAX is aluminum hydroxide. If the vials are filled unevenly, and the deviation is +42%, then 0.5 mL will contain 0.852 mg or more Al(III), which exceeds the federal limit. Advantageously, a 42% (or more) deviation, i.e., a filling error, is easily detected using the methods described herein.

The present inventors have thus disclosed an in situ, real-time in-line, contact-less quality control method using solvent NMR to determine if a filling error has occurred during the fill-finish unit operation to deliver alum-containing product, e.g., vaccines, from an upstream large-scale product vessel to the product container (e.g., vial). This allows for the manufacturer to monitor for unexpected anomalies or errors, e.g., too much or too little alum adjuvant, batch-to-batch variations of the same product, and/or clogs in the filling conduit and/or exposure to at least one stressor. This can be done without pulling any of the alum-containing product out of the filling conduit. Further advantages include the applicability of the method for both continuous and batch unit manufacturing operations, both anti-bacterial and anti-viral vaccines, and/or both drug products and drug substances.

The methods described herein relate to the determination if a filling error has occurred during the fill-finish unit operation associated with alum-containing products. It should be understood by the person skilled in the art that the flow wNMR method described herein can be used at other points in the manufacturing process, for example, to verify concentration of reactants and/or intermediates as they are delivered to, or removed from, their respective steps in the chemical and physical reactions. In addition, the flow wNMR method described herein can be used to detect the clustering of aluminum particles, whether in the filling conduit or in the reaction/storage vessel. Further, it should be appreciated by the person skilled in the art that the methods described herein are not limited to the manufacturing of alum-containing products but can be used to identify filling errors associated with pharmaceutical product manufacturing in general.

In addition, as introduced hereinabove, the manufacturer will understand how to prepare and use calibration curves. The calibration curves can be used when the manufacturer requires a different flow rate or concentration of Al(III) for delivery, wherein the slope of the calibration curve can be used to determine the reference transverse relaxation rate of solvent $R_{2,r}$. The calibration curve is also useful as a standard as new facilities or manufacturing tracks are brought online.

The features and advantages of the invention are more fully shown by the illustrative examples discussed below.

Example 1

Materials and Sample Preparation

Two aluminum vaccine adjuvants—aluminum hydroxide gel (ALHYDROGEL, [Al(III)] 10 mg/mL) and aluminum phosphate gel (ADJU-PHOS, [Al(III)] 5 mg/mL (Brenntag Biosector S/A (Denmark))—were used.

Initial suspensions of both adjuvants were diluted with pure water (18.2 MOhm) to form a series with Al(III) concentrations of 5.0 mg/mL, 2.0 mg/mL, 1.0 mg/mL, and 0.5 mg/mL. Fifty mL of each diluted sample were aliquoted into 50 mL polyethylene centrifuge tubes used to fill the flow loop of the flow NMR set-up.

Monitoring, Calculations, and Results

The water proton transverse relaxation time $T_2(^1H_2O)$ at different flow rates was measured using benchtop wide through-bore time-domain SpinTrack NMR at 0.37 T, 15.9 MHz resonance frequency for $^1H$ (Resonance Systems GmbH, Kirchheim/Teck, Germany). The magnet temperature was set to 29.5° C. while the room temperature was maintained at 18° C. Continuous flow was generated using a digital peristaltic pump (MasterFlex L/S, Cole-Parmer, Vernon Hill, Illinois) with up to four channel connections to compensate for flow pulsations. The flow loop was completed by the flow tube inserted inside the magnet. The magnet bore size is 40 mm and the total length of the magnet is 18 cm. The length of the duplex RF-coil (transmitter-receiver) is 5 cm, thus, the remaining 13 cm of the probe serve as a prepolarization zone. The flow tube was a cylindrical PTFE tube (tube o.d. 9 mm, tube length 40 cm). About 50 mL of a sample was circulated through the flow system (flow loop outside the magnet +flow tube inside the magnet), and $T_2(^1H_2O)$ was measured at different flow rates. The sample temperature was equilibrated to room temperature which was kept stable at 18° C.

A standard Carr-Purcell-Meiboom-Gill (CPMG) pulse sequence (Meiboom, S., et al., 1958) was used in $T_2(^1H_2O)$ measurements. Two transients were collected with a relaxation delay of 8 s, interpulse delay of 300 µs with number of echoes collected from 2500 (for highest adjuvant concentrations) to 10,000 (for lowest adjuvant concentrations). The built-in Relax8 software (Resonance Systems GmbH, Kirchheim/Teck, Germany) was used to extract $T_2(^1H_2O)$ values using a mono-exponential fit of the decay of the $^1H_2O$ echo signal using Equation (1):

$$I(t) = I_0 \exp[-t/T_2(H_2O)] \tag{1}$$

where I(t) is the observed decay of echo signal intensity over echo decay time t, $I_0$ is the initial echo signal intensity at t=0. Measurements for each sample were done in triplicate, and the resulting plotted values of water proton transverse relaxation rate $R_2(^1H_2O)$ (where $R_2(^1H_2O)=1/T_2(^1H_2O)$) are the arithmetic means with standard deviation used as an error bars in the plots. The range of flow rates was from 0 to 50 mL/min.

Figure 2A:
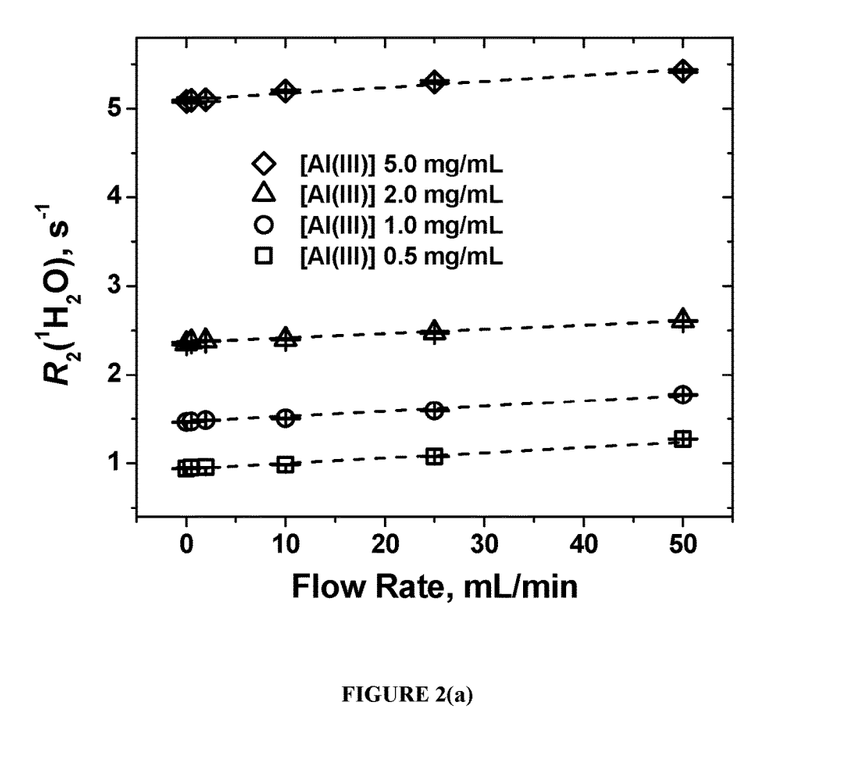
FIG. 2(a) shows the dependences of the water proton transverse relaxation rate $R_2(^1H_2O)$ on the flow rates from 0 to 50 mL/min, for samples of ALHYDROGEL at adjuvant concentrations [Al(III)]0.5 mg/mL, 1.0 mg/mL, 2.0 mg/mL, and 5.0 mg/mL. Error bars reflect standard deviation of three consecutive measurements. Average slope of the linear dependencies is $(0.0060\pm0.0001)$ $s^{-1}L^{-1}$min.
Figure 2B:
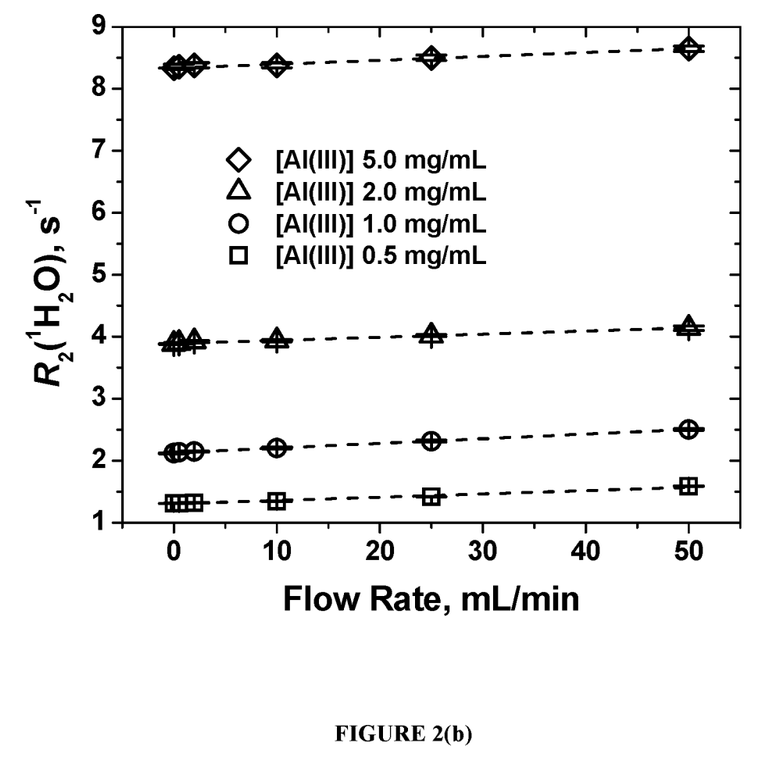
FIG. 2(b) shows the dependences of the water proton transverse relaxation rate $R_2(^1H_2O)$ on the flow rates from 0 to 50 mL/min, for samples of ADJU-PHOS at adjuvant concentrations [Al(III)]0.5 mg/mL, 1.0 mg/mL, 2.0 mg/mL, and 5.0 mg/mL. Error bars reflect standard deviation of three consecutive measurements. Average slope of the linear dependencies is $(0.0057\pm0.0001)$ $s^{-1}mL^{-1}$min.

Flow dependences of $R_2(^1H_2O)$ for both ALHYDROGEL and ADJU-PHOS adjuvants at different concentrations demonstrated the sensitivity of flow water proton NMR to flow rates in the range from 0 mL/min to 50 mL/min (FIGS. 2(a) and 2(b)). Linearity of the dependences shown in FIGS. 2(a) and 2(b) facilitates the detection of flow rate changes under the settings of continuous manufacturing of adjuvanted vaccines, e.g., in case of clogging leading to abrupt flow changes. The values of the slopes of linear dependences (~0.0060 and 0.0057 $s^{-1}$ $mL^{-1}$min) allows the user to noninvasively detect flow rate changes as low as about ±2 mL/min. Calibration curves can be prepared by the user, as readily understood by the person skilled in the art.

Figure 3A:
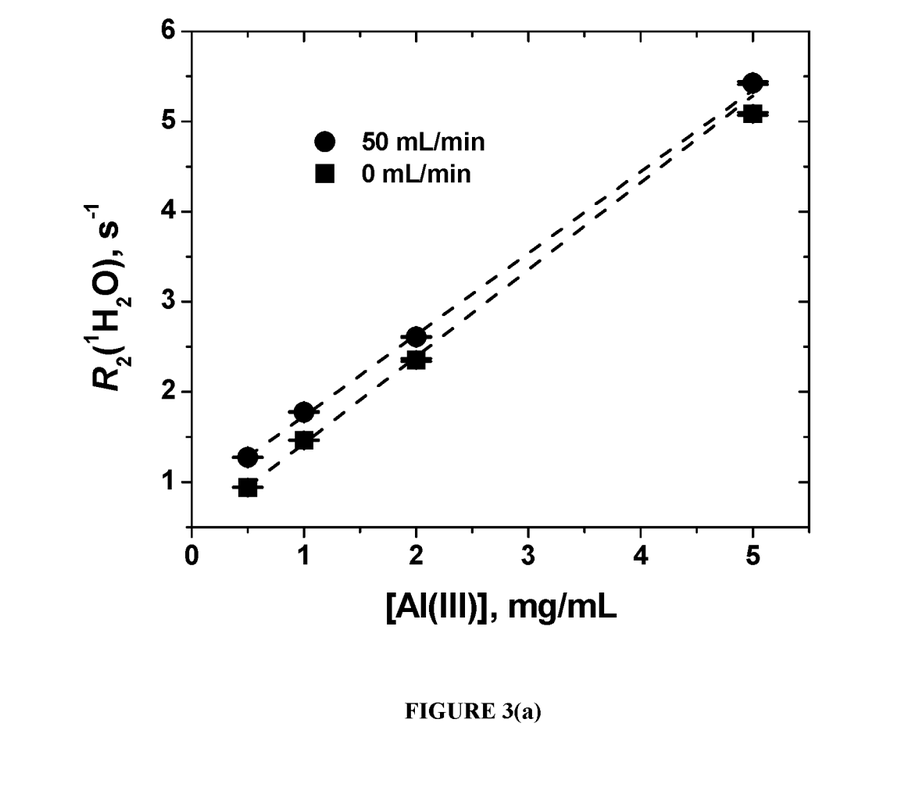
FIG. 3(a) shows the dependences of the water proton transverse relaxation rate $R_2(^1H_2O)$ on the concentration of ALHYDROGEL samples in the range of [Al(III)] 0.5 mg/mL to 5.0 mg/mL at two flow rates (0 mL/min and 50 mL/min). Error bars reflect standard deviation of three consecutive measurements. Average slope of the linear dependencies is $(0.950\pm0.015)$ $s^{-1}mg^{-1}$ mL.
Figure 3B:
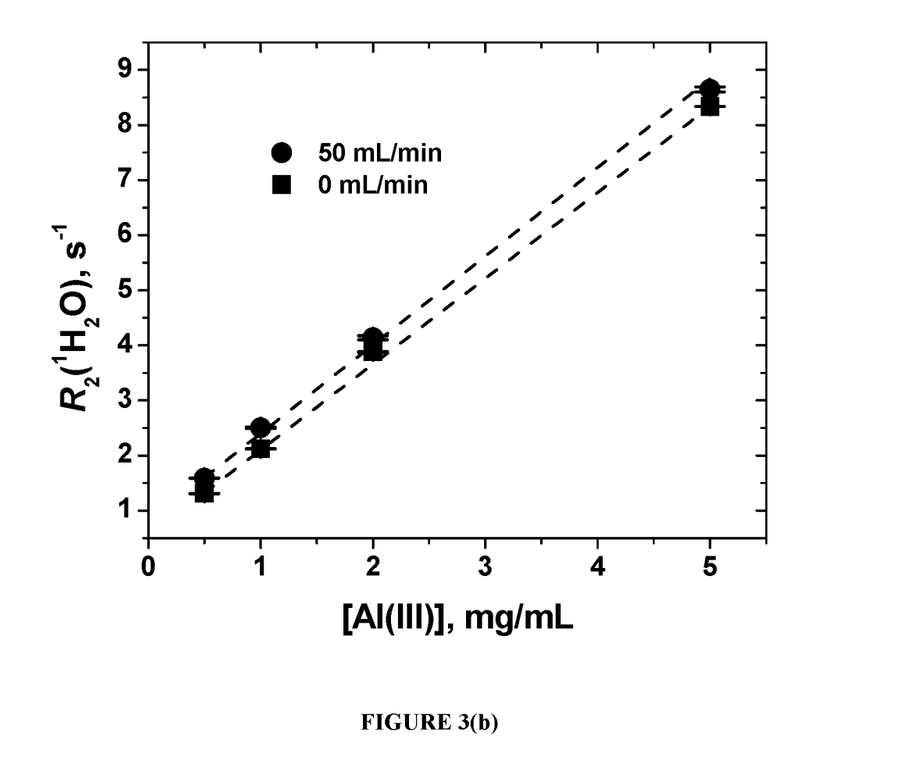
FIG. 3(b) shows the dependences of the water proton transverse relaxation rate $R_2(^1H_2O)$ on the concentration of ADJU-PHOS samples in the range of [Al(III)] 0.5 mg/mL to 5.0 mg/mL at two flow rates (0 mL/min and 50 mL/min). Error bars reflect standard deviation of three consecutive measurements. Average slope of the linear dependencies is $(1.584\pm0.030)$ $s^{-1}$ $mg^{-1}$ mL.

In addition, as seen from FIGS. 3(a) and 3(b), $R_2(^1H_2O)$ under flow conditions shows strong response to changes in concentration for both ALHYDROGEL and ADJU-PHOS adjuvants. Linear response to concentration observed under flow conditions allows one to use flow water proton NMR to monitor variations of an adjuvant concentration under settings of continuous manufacturing of adjuvanted vaccines. The values of the slopes of linear dependences (~0.950 and 1.584 $s^{-1}$ $mg^{-1}$mL) allows to detect adjuvant concentration changes as low as ±0.01 mg/mL-noninvasively and under flow conditions. Calibration curves can be prepared by the user, as readily understood by the person skilled in the art.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

Baylor, N. W., Egan, W., Richman, P., (2002) Aluminum salts in vaccines—US perspective. *Vaccine*, 20, S18-S23.

Briggs, K. T., Taraban, M. B., Yu, Y. B. (2018) Water proton NMR detection of amide hydrolysis and diglycine dimerization. Chem. Comm. 54, 7003-7006.

Khatun, R., Hunter, H. N., Sheng, Y., Carpick, BW., Kirkitadze, M. D., (2018) $^{27}$Al and $^{31}$P NMR spectroscopy method development to quantify aluminum phosphate in adjuvanted vaccine formulations. *Journal of Pharmaceutical and Biomedical Analysis*, 159, 166-172.

Lindblad, E. B., (2004) Aluminum compounds for use in vaccines. *Immunology and Cell Biology*, 82. 497-505, 82.

Metz, H., Mäder, K., (2008) Benchtop-NMR and MRI—a new analytical tool in drug delivery research, *Int. J. Pharm.*, 364, 170-178.

Mishra, A., Bhalla, S. R., Rawat, S., Bansal, V., Sehgal, R., Kumar, S., (2007) Standardization and validation of a new atomic absorption spectroscopy technique for determination and quantitation of Aluminium adjuvant in immunobiologicals. *Biologicals*, 35, 277-284.

Petrovsky, N. (2015) Comparative safety of vaccine adjuvants: a summary of current evidence and future needs. Drug Safety, 38, 1059-1074.

Rohrer, M, Bauer, H., Mintorovitch, Jan., Requardt, M., Weinmann, H. J., (2005) Comparison of magnetic properties of MRI contrast media solutions at different magnetic field strengths. Invest. Radiol. 40, 715-724.

Vecchi, S., Bufali, S., Skibinshi, D. A. G., O'hagan, D. T., Singh, M. (2011) Aluminum adjuvant dose guidelines in vaccine formulation for preclinical evaluations. J. Pharm. Sci. 101, 17-20.

Yu, Y. B., Feng, Y., Taraban, M. B. (2017) Water proton NMR for noninvasive chemical analysis and drug product inspection. Am. Pharmaceut. Rev. 20, 34-39.

What is claimed is:

1. A method of detecting a filling error of an alum-containing product in real-time and in-line during a fill-finish unit operation, said method comprising:
   introducing the alum-containing product into a filling conduit, wherein the filling conduit directs the alum-containing product into a vial, and wherein the filling conduit is arranged to pass through a magnet of a nuclear magnetic resonance (NMR) spectrometer prior to reaching the vial;
   measuring a transverse relaxation time of water $T_{2,m}$ in the alum-containing product passing through the filling conduit; and
   comparing the measured $T_{2,m}$ to a reference transverse relaxation time of water $T_{2,r}$, wherein $T_{2,r}$, is a range which is considered an acceptable flow rate or concentration of aluminum particles in the alum-containing product,
   wherein when the measured $T_{2,m}$ is within the range of the reference $T_{2,r}$, there is no filling error.

2. The method of claim 1, wherein the filling conduit delivers the alum-containing product from an upstream large-scale product vessel to the vial.

3. The method of claim 1, wherein the $T_{2,m}$ is measured without withdrawing the alum-containing product from the filling conduit.

4. The method of claim 1, wherein the alum-containing product comprises particles in a range from 1 nanometer to 50 microns in diameter.

5. The method of claim 1, wherein the alum-containing product comprises aluminum-containing salts selected from the group consisting of aluminum hydroxide, aluminum phosphate, alum ($KAl(SO_4)_2·12H_2O$), aluminum hydroxyphosphate sulfate, and any combination thereof.

6. The method of claim 1, wherein the alum-containing product is a vaccine comprising an alum adjuvant or a pharmaceutical product comprising aluminum particles.

7. The method of claim 1, wherein the filling error is selected from the group consisting of a clog in the filling conduit, non-homogeneous mixing of a concentrated alum-containing suspension with a diluent upstream of the filling conduit, accidental exposure of the alum-containing product to a stressor, and any combination thereof.

8. The method of claim 7, wherein the stressor is selected from the group consisting of a temperature fluctuation, a pH change, vigorous mixing, an ionic strength change, presence of a contaminant, freezing, and any combination thereof.

9. The method of claim 1, wherein the alum-containing product comprises particles in a range from 500 nm to 1000 nm.

10. The method of claim 1, wherein $T_{2,m}$ and $T_{2,r}$, are measured at a substantially similar the same temperature.

11. The method of claim 1, wherein manufacturing operations are selected from continuous or batch unit.

12. The method of claim 1, wherein the alum-containing product comprises particles in a range from 1000 nm to 5000 nm.

13. The method of claim 1, wherein the alum-containing product comprises particles in a range from 1000 nm to 10000 nm.

\* \* \* \* \*